United States Patent [19]

Pritchard

[11] Patent Number: 4,491,725

[45] Date of Patent: Jan. 1, 1985

[54] MEDICAL INSURANCE VERIFICATION AND PROCESSING SYSTEM

[76] Inventor: Lawrence E. Pritchard, 2517 Wellington Rd., Cleveland Heights, Ohio 44118

[21] Appl. No.: 426,982

[22] Filed: Sep. 29, 1982

[51] Int. Cl.³ .............................................. G06F 3/00
[52] U.S. Cl. ................................... 235/375; 235/378; 235/380; 364/413
[58] Field of Search ............... 235/377, 375, 376, 383, 235/385, 451, 432, 449, 471, 380; 194/DIG. 9; 364/413, 415, 406, 401, 403, 464, 436

[56] References Cited

U.S. PATENT DOCUMENTS

| | | | |
|---|---|---|---|
| 3,679,175 | 7/1972 | Rawson et al. | 235/375 |
| 3,921,196 | 11/1975 | Patterson | 235/375 |
| 3,935,427 | 1/1976 | Geul | 235/375 |
| 4,135,241 | 1/1979 | Stanis et al. | 364/200 |
| 4,212,069 | 7/1980 | Baumann | 364/467 |
| 4,247,759 | 1/1981 | Yuris et al. | 235/381 |
| 4,277,837 | 7/1981 | Stuckert | 364/900 |
| 4,346,442 | 8/1982 | Musmanno . | |
| 4,359,631 | 11/1982 | Lockwood et al. | 235/381 |
| 4,360,875 | 11/1982 | Behnke | 364/436 |
| 4,370,649 | 1/1983 | Fuerle | 340/825.35 |
| 4,408,181 | 10/1983 | Nakayama | 82/61 |

OTHER PUBLICATIONS

J. M. Braendler, "A Computer Controlled Telemetry System", Conference—May 10-14, 1976—I.E.A.A.N.
Alex. Brown & Sons, "Shared Medical Systems Corp. Health Care Group", May 1982.
"Health Care Provider Information", N.E.I.C., 1982.
E. Fabo & E. Hoglund, "C.T.R–Computerized Time Recording", Ericsson Review, No. 2, 1980.
Bert Latamore, "The Smart Card", Desktop Computing, Aug. 1982, pp. 46–51.

"Tymshare Medical Systems" advertisement.

*Primary Examiner*—Stafford D. Schreyer
*Assistant Examiner*—Robert G. Lev
*Attorney, Agent, or Firm*—Richards, Harris & Medlock

[57] ABSTRACT

A medical claim verification and processing system reads a medical information card (MEDICARD) to determine a patient's background medical and insurance information. The validity of the card is rapidly determined by accessing a central brokerage computer. A local service provider enters into a local terminal the medical and MEDICARD information services provided or to be provided to the patient by using a patient service code and transmits this information to a central brokerage computer. The central brokerage computer converts the patient service code input by the service provider or MEDICARD into a particular service code for the patient's insurance carrier. This service code is then utilized to determine the insurance claim payment for that particular patient service. The claim payment amount for the medical service is then transmitted back to the local entry terminal for use by the service provider and patient. The service provider and patient can then determine the amount of payment which will be made for the particular insurance claim. The provider can then prepare an electronic claim form and, together with the patient's and/or the provider's determination whether or not the assignment provision of the insurance claim will be invoked, the electronic claim form is then transmitted to a central brokerage computer which in turn transmits the claim form to the appropriate insurance carrier. The patient's insurance carrier processes the claim form, and, based upon the assignment decision, transfers the payment check to the patient or makes an electronic funds transfer to an account for the service provider, the patient or a central brokerage computer.

21 Claims, 10 Drawing Figures

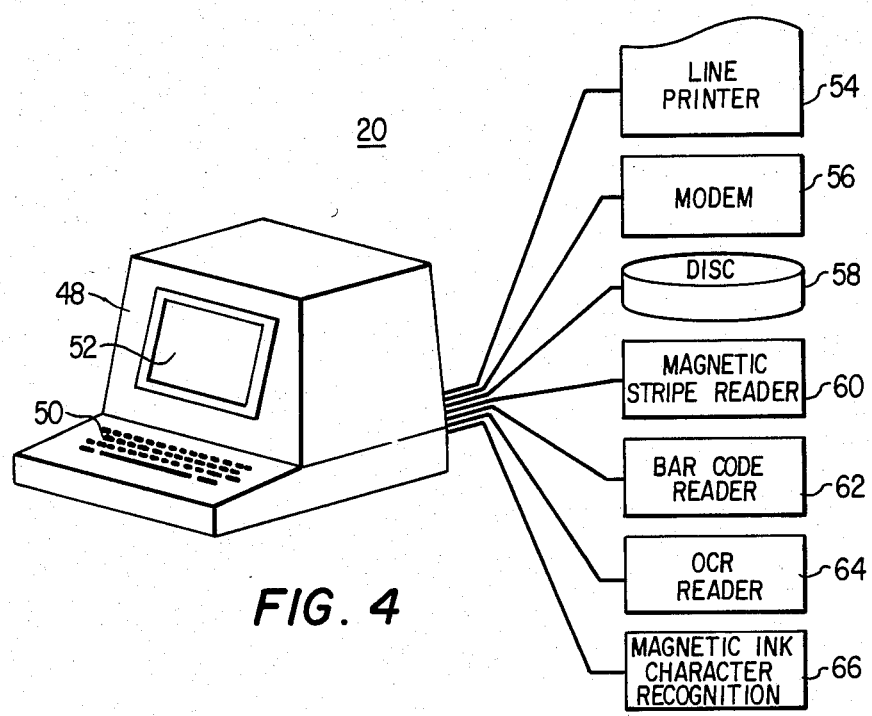

MEDICAL INSURANCE VERIFICATION AND PROCESSING SYSTEM

TECHNICAL FIELD

The present invention pertains in general to data processing, and more particularly to the evaluation of medical insurance coverage, the determination of claim payment schedules, and the processing of insurance claim payments.

BACKGROUND OF THE INVENTION

Most people are now covered by some form of public or private medical insurance and a substantial portion of all medical fees are paid through such insurance. In the context of the patient and the physician or any other health care provider relationship, it is the typical procedure for the provider to bill the patient for the full cost of the service with the patient or service provider then filing a claim with his insurance carrier for reimbursement of part or all of the service fee. The routine processing of an insurance form can take many weeks and it can be a substantial time before the patient or medical service provider receives a reimbursement for the medical expense. In most cases, the insurance claim forms are complex and difficult for both patients and medical providers to understand. There is a substantial likelihood that mistakes can be made in the preparation of the forms. When such mistakes are made, there is a still further delay in the processing of the claim for payment to the patient or health care provider.

For many patients it is financially difficult to make a fee payment to the service provider prior to receiving payment from the insurance carrier but the service provider desires to receive his payment on a prompt basis. Therefore, the difficulty in filing and reimbursement of insurance claims serves to work a hardship for both the health care provider and the patient.

Many insurance companies include a provision in their claim form for the assignment of the insurance claim payment from the patient to the service provider. An intent of this assignment is to relieve the patient of the immediate burden of that portion of the service provider's fee which will be reimbursed by insurance. In practice, however, the assignment provision of insurance claims has proven to be of limited benefit to either the patient or medical service provider, since many service providers demand some immediate form of payment at time of service. At present, there exists no simple system or method whereby either a patient or health care provider has instant accessibility to a multitude of insurance claim payment schedules for medical services. It is difficult, therefore, for patients and/or health care providers to make an assignment decision on an insurance claim payment because the insurance claim payment information is not readily available to both parties involved in the insurance claim assignment provision.

Insurance carriers develop fee payment schedules which determine the fee that they will pay for each particular type of service. These tables are generally complex and involve hundreds of items with the fee payment for each item dependent upon several factors such as deductibles, accident only exclusions and time related factors which affect reimbursement to both patients and health care providers. With the exception of government managed insurance programs, fee payment schedules are not made easily available to patients or health care providers. However, these fee payment schedules are available. Thus, when a health care provider renders a service to a patient and a claim form is prepared, the health care provider may be, or is often reluctant to accept the claim assignment provision of the insurance payment since in most cases neither the physician nor the patient knows the amount that the insurance carrier will pay for the service. As a result, a health care provider cannot determine the differential, if any, between the insurance payment and his fee charge to determine how much to bill the patient. As a result of this lack of knowledge, some or most health care providers are often unwilling to agree to the assignment provision of an insurance claim. This, in turn, works a hardship for patients who are asked by health care provider's to pay for their services rendered at the time of service. Low income patients and elderly patients on fixed incomes particularly are affected when they must pay the full service fee. If the health care provider or patient agrees to the assignment provision, the provider must await the slow processing of the insurance forms and the preparation of a payment check which the provider must first receive before he can determine if there is any additional billing to be made to the patient.

In view of the above problems relating to the assignment provision of insurance claims and the difficulties in processing insurance claim forms, there exists a need for a method of rapidly determining the reimbursement of an insurance company's claim amount which will be paid by a specific insurance carrier to a patient or a health care provider for a particular service. This amount should be determined while the patient is still present in the service provider's office. If the health care provider and the patient could be given a method by which either party is able to determine the amount of the insurance claim reimbursement for a particular service, either party, i.e., the doctor or patient can make a better reasoned business decision to facilitate agreement to the insurance assignment provision. As a result, the patient will have a substantially reduced immediate payment for the service, or possibly no payment at all. Although the insurance assignment and claim processing problems are particularly relevant to the physician-patient relationship, these problems are also present in other health care areas such as hospitals, clinical laboratories, supplying of durable medical equipment (DME) and nursing homes.

As health care costs for hospital and medical service provider related services continue to rise under both private and government-managed health insurance plans, "cost containment" in the health care field becomes a problem that our society must address.

One method by which both private and government-sponsored insurance plans are currently dealing with "cost containment" is requesting that their subscribers receive cost amount "bids" or "claim payment amounts" for medical treatments or services from different health care providers i.e. doctors, hospitals, or medical suppliers, before certain services or treatments are rendered.

A cost-control mechanism is therefore needed to help with "cost containment" in the health care field, without, of course, destroying the needs under the free enterprise system or the private relationship which must be maintained between insurance carriers, patients and various health care providers.

There is a need for greater interaction and dissemination of medical cost information to all parties involved in the present health care field for supporting cost containment measures. The greater dissemination of health care information for cost control serves the benefit of:
(1) Patients
(2) Health care providers (doctors, laboratories, etc.)
(3) Insurance carriers
(4) Hospitals
without destroying any existing "freedom of choice" relationships which exist under our present system of health care management.

There also exists a lack of knowledge and understanding by both patients and medical health care providers as to the validity and provisions or limits of coverage of medical benefits under a certain particular insurance carrier's policy.

Because of this lack of knowledge and the complexities of whether or not a particular insurance policy is valid or current, and because of the ever-changing regulations by both private and government managed medical insurance plans, there exists a need for a method by which both health care provider, i.e., hospital, doctor, etc., and the patient can be rapidly informed as to the validity of coverage and benefits under one or more of the patient's health care insurance plans.

SUMMARY OF THE INVENTION

A selected embodiment of the present invention comprises a method for rapidly determining an insurance claim payment for a specified payment service. A file is stored in a system memory for each of a plurality of insurance carriers with each file having a set of service codes with a claim payment for each service code. A code conversion table is stored in a system memory for each of the insurance carriers for converting patient treatment codes into service codes for the corresponding insurance carrier. The patient treatment codes correspond respectively to patient services. The name for a selected patient and a selected one of the treatment codes are transmitted through a system input device. Next, the selected patient's insurance carrier is determined. The code conversion table is machine read for the selected patient's insurance carrier to translate the selected treatment code into the corresponding service code for the patient's insurance carrier. The file for the patient's insurance carrier is machine read to determine the claim payment for the service code which was produced by the translation of the patient treatment code. Finally, there is displayed via a system output device the determined claim payment for the specified payment service for the selected patient.

BRIEF DESCRIPTION OF THE DRAWINGS

For a more complete understanding of the present invention and the advantages thereof, reference is now made to the following description taken in conjunction with the accompanying drawings in which:

FIG. 4 is an illustration of a local entry terminal for installation in a health care provider's office for assisting in the evaluation of insurance coverage and in the preparation of insurance claim forms, FIG. 5 is an illustration of a patient file containing vital medical and insurance information for a patient, FIG. 6 is an illustration of an insurance carrier file which relates service codes to insurance claim payments.

FIG. 7 is a code conversion table for an insurance carrier which relates a standardized service code, such as provided by the American Medical Association, to a specific service code set utilized by an insurance carrier, FIG. 8 is an illustration of a display for the screen of the apparatus shown in FIG. 4 to indicate the validity of insurance coverage for a particular patient and the claim payment for a particular service provided by a health care provider.

DETAILED DESCRIPTION OF THE INVENTION

Figure 1:
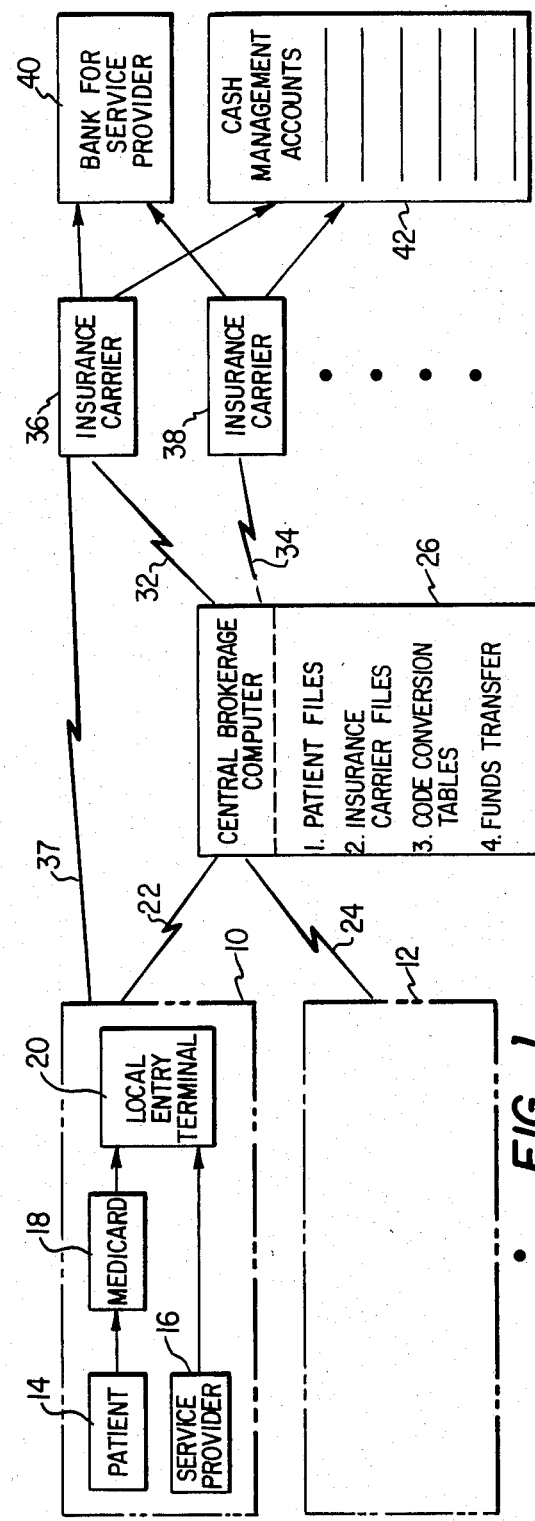
FIG. 1 is a block diagram illustrating the relationships of the entities and the parties involved in the processing of insurance claim forms for showing the method of operation of the present invention.

Referring now to FIG. 1 there is illustrated a block diagram showing the relationship of the various persons and entities involved in the verification and processing of insurance claim payments in accordance with the method of the present invention. There are illustrated a plurality of local sites 10 and 12 each of which represents a local office that directly renders medical services to an individual. A preferred example of such a local site is a doctor's office. However, this could also be the location of a hospital, a supplier of durable medical equipment, a hospital emergency room, an ambulatory surgical clinic, a clinical laboratory, a nursing home, etc.

Within the local site 10 there is included a patient 14 and a service provider 16. In the preferred embodiment of the present invention the patient is provided with a medical and insurance identification card termed a MEDICARD 18. The MEDICARD 18 is further illustrated in FIGS. 2 and 3.

Information from the MEDICARD 18 is entered into a local entry terminal 20, which is described in detail below. Additional information, concerning the services provided to the patient 14, are input by the service provider 16 into the local entry terminal 20.

The local sites, such as 10 and 12, are connected via telecommunication links 22 and 24 respectively to a central brokerage computer 26. The central brokerage computer 26 is typically located at a remote site some distance from the local sites 10 and 12. The computer 26 stores files and tables as described below and can serve to provide funds transfer between the various parties and their financial accounts. The operation of the computer 26 can be operated by previous agreement as an agent of the parties to carry out the required funds transfers.

The central brokerage computer 26 is connected via telecommunication links 32 and 34, respectively, to a plurality of insurance carriers such as 36 and 38. There may be any number of such insurance carriers. These insurance carriers can be either private or government-established entities such as MEDICAID or MEDICARE carriers of Part A or Part B services.

The local sites can also communicate directly to the insurance carriers such as site 10 communicating through a telecommunications link 37 to the insurance carrier 36.

Each of the insurance carriers, such as 36 and 38, can communicate to a bank 40 or an institution 42 which provides services such as CASH MANAGEMENT ACCOUNTS (registered trademark of Merril-Lynch & Co.). Such an account is described in U.S. Pat. No. 4,346,442 to Musmanno.

The bank 40 is illustrated to be the bank of the service provider but it could also be the bank for the patient 14. The institution 42 can be used by both the patient 14 and service provider 16.

Figure 3:
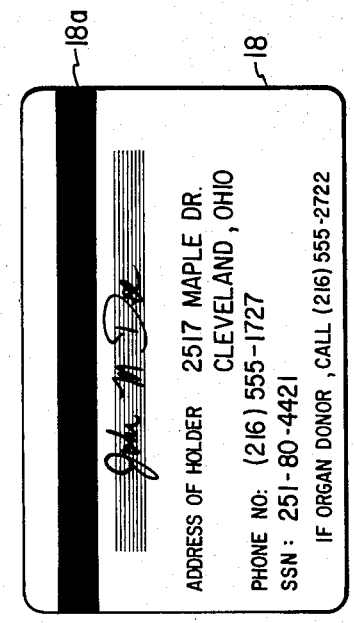
FIG. 3 is an illustration of the back of a standardized medical card for use in conjunction with the method of the present invention.
Figure 2:
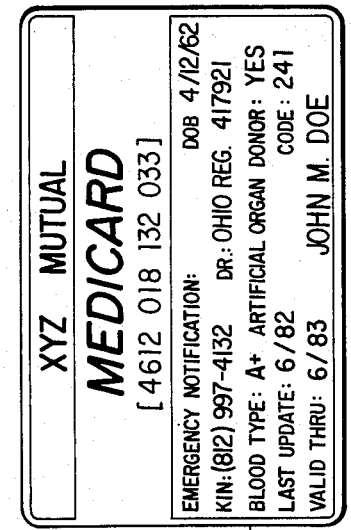
FIG. 2 is an illustration of the front of a standardized medical card for use in conjunction with the method of the present invention.

The MEDICARD 18 is further described in reference to FIGS. 2 and 3. In a preferred embodiment the MEDICARD 18 is a plastic card, corresponding in size to a conventional credit card, and having a magnetic stripe on the back thereof. The MEDICARD 18 includes information both printed on the surfaces of the card and electronically coded on the card, such as in the magnetic stripe. As shown in FIG. 2, the information written or embossed on the face of MEDICARD 18 includes the name of the patient, the patient's insurance carrier, date of birth, the patient's MEDICARD number, telephone emergency notification for relatives and doctor, blood type, artifical organ donor status, the date of last update of the information on the card and the valid thru date of the card.

On the back of the MEDICARD 18, as shown in FIG. 3, there is printed or embossed the patient's address, telephone number and social security number as well as an organ donor telephone notification number. Stored on the card electronically in a magnetic stripe 18a or in a computer memory chip in the MEDICARD 18 is various information concerning the patient.

The information which is stored on the magnetic stripe of the MEDICARD 18 is preferably organized in three security levels. By use of the three security levels certain parties and persons can be limited to the information which they can obtain from the card. In the first security level there is recorded on the card the name of the insured party, his social security number, his address and telephone number, as well as any other personal identification data such as marriage status and sex. There is further included the name of his insurance carrier, including any secondary or tertiary carriers, supplemental insurance carriers as well as the specific policy numbers for these insurance carriers, i.e. Medicare Hospital coverage Part A, Medicare Medical coverage Part B. At the second security level, there is included a security clearance, such as a flight security status to indicate any unusual condition related to flying such as the implentation of a metal prosthesis, the patient's need for any particular type of medication and any critical medical problems which could be experienced by the patient. At the third security level there is stored specific clinical data for the patient including his detailed medical history. The various security levels serve to protect the privacy of the patient by limiting access to personal information to only those parties who require such information and are authorized to receive it.

As noted above, the MEDICARD 18 can be similar to a conventional credit card or, for greater information storage and security, it can be what is termed a "smart-card" which is a similar-sized card having an integrated circuit chip molded therein and accessible thereto by means of an appropriate communication device. The integrated circuit chip in the "smart card" can both store, update and process information and is described in "Desktop Computing", Aug. 1982 at pp. 46-51.

The local entry terminal 20 is described in further detail in FIG. 4. The terminal 20 includes a data terminal 48 which has a keyboard 50 for entering information into the terminal 48 and a display 52 for displaying information stored in the terminal 48. The terminal 48 is connected to a line printer 54, a modem 56, a storage disc 58, a magnetic stripe reader 60, a bar code reader 62 and an optical character recognition (OCR) reader 64. The magnetic stripe reader 60 is adapted to read the magnetically coded information on the MEDICARD 18. The reader 62 is for inputting information which is printed in the bar code standard format. The reader 64 can read printed text and eliminate the need for specially coded forms. A selected embodiment for the OCR reader 64 is an NCR Model 7887 OCR-A. A device 66 is a magnetic ink character recognition device (MICR) which has the capability of reading signatures.

A patient file 68 is illustrated in FIG. 4. The file 68 comprises a collection of information for a specific patient. This information includes, but is not limited to, the patient's name, address, details of insurance coverage and medical history. The file 68 can be stored at either the local site such as 10, within the MEDICARD 18 or in the central brokerage computer 26 or at a plurality of these locations.

FIG. 6 is an illustration of a file 70 for a specific insurance carrier, such as carriers 36 and 38 shown in FIG. 1. The file 70 for each insurance carrier has a first set of numbers for example, four digits, which correspond to service codes for that particular insurance carrier. Each of the service codes defines a particular type of patient service delivered by a health provider. This can be either a treatment or the provision of a medical apparatus. For each of the four digit service codes there is provided a corresponding maximum insurance claim payment for the particular service code. The service codes may or may not be uniform for all of the insurance carriers. The payments for the services can vary also from carrier to carrier.

FIG. 7 is an illustration of a code conversion table 72 for a particular insurance carrier. In the left column there are listed standard patient treatment codes, such as those issued by the AMA and termed CPT-IV (Current Procedural Terminology) codes. For each of the CPT-IV codes there is listed a corresponding four digit service code for the given insurance carrier. Thus, the standardized AMA CPT-IV code can be converted by means of Table 72 into a specific service code for the given insurance carrier.

FIG. 8 is an illustration of a display at the terminal 20 to show the maximum claim payment for at least a selected patient treatment together with displaying at least the patient's name and insurance carrier.

The operation of a first embodiment of the present invention is now described in reference to FIGS. 1-8. The patient 14 receives a specified service from the provider 16 at the local site 10 or desires to inquire from a provider 16 about the cost and insurance coverage for a specific medical-related service. As noted above, it is typically the practice that a patient, after receiving a medical service from a service provider, immediately pay the entire service fee to the service provider 16. Typically, as stated above, it is not feasible for the service provider or patient to take advantage of the assignment provision of the insurance claim since the amount of such payment is not known to either the patient or the service provider.

In the preferred embodiment of the present invention, the patient 14 is issued the MEDICARD 18 by his insurance carrier 36 or by another party such as an insurance broker. This card contains security related and pertinent vital personal, medical and insurance information. While the patient 14 is at the local site 10, the MEDICARD 18 is entered into a reader, such as reader 60 shown in FIG. 4, and the basic information regarding the patient's name and insurance coverage are read from the card. The patient's insurance policy number or type of insurance is read electronically or visually at the local entry terminal 20 and transmitted via the telecommunications link 22 to the central brokerage computer 26. At the central brokerage computer 26 the information received from the local entry terminal 20 is checked against master patient files as described above, to determine if the patient 14 has current insurance coverage and if the patient's MEDICARD 18 is valid. After this check is made, a return verification is transmitted via link 22 to the local entry terminal 20. There is then produced on the display 52 a basic yes/no validation of the MEDICARD 18. If the display indicates that the patient's card is valid, the service provider 16 can be confident that the patient 14 is covered by current insurance and that the information as it presently exists on the MEDICARD matches with the current brokerage computer 26 master files. If the report shows that the insurance is not current or valid, the service provider 16 and patient 14 are made aware that at least the patient's insurance coverage is not current or valid.

In the next step, the service provider 16 calls up via keyboard 50 to the display 52 a standardized insurance claim form which has been stored, such as for example, on the disc 58. The standardized claim form can, for example, correspond to the HCFA (Health Care Finance Administration) form 1500. The appropriate information is entered into this form. A substantial amount of information regarding the patient and his insurance carrier is derived directly from the MEDICARD 18 and/or manually. The remaining information, which must be manually entered through any of the input devices 60–66 shown in FIG. 4 by the service provider 16, is concerned with the specifics of the diagnosis and treatment provided by the service provider 16 to the patient 14. Thus, the standardized form can be rapidly completed without the need for querying the patient in regard to detailed information concerning claim and group numbers for his insurance. The health care service provider (16) can also rapidly complete the claim form by entering further patient disease and treatment information manually or using manual electronic time-saving devices as those shown at local entry terminal 20. The service provider (16) may also choose to enter certain displayed information from terminal 48 after reading the MEDICARD 18, at the local entry site 10, and this, too, will allow rapid completion of the standardized insurance claim form.

The standardized claim form is completed in all respects except for the entry of a yes/no regarding the assignment provision of the insurance payment to the service provider or to the patient. The form is then transmitted electronically via the telecommunications link 22 to the central brokerage computer 26. At the computer 26, the form is examined to determine if it has been correctly prepared to meet the requirements of the patient's insurance carrier. If an error is detected in the form, an appropriate error message is sent from computer 26 via link 22 to the local terminal 20. The service provider 16 can then correct the form and send the corrected form to the central brokerage computer 26. Optionally, the electronic claim form can be evaluated locally without using the computer 26.

When a correctly prepared claim form is received by the computer 26 from the terminal 20, the CPT-IV code, which was entered by the service provider into the standard form, is converted by use of Table 72 for the appropriate insurance carrier, herein labeled XYZ Mutual. Table 72 converts the five digit CPT-IV code into a four digit service code for the selected insurance carrier. Next, the file for that particular carrier, such as file 70 shown in FIG. 6, is referenced with the selected service code. This service code is then utilized to read the claim payment for that particular service code. This claim payment amount is then transmitted, together with a control number for the particular claim, via the telecommunications link 22 back to the local entry terminal 20. The data terminal 48 utilizes the information previously received from the MEDICARD 18, the CPT-IV code or codes entered by the service provider and the information received from the central brokerage computer 26 to produce a display 78 as shown in FIG. 8. The display 78 shows the patient's name, the service provided by the service provider 16, the name of the patient's insurance carrier, and the claim payment that the patient's MEDICARD-specified insurance carrier coverage will allow for the particular service performed or inquiry provided in behalf of the doctor or patient. This claim payment amount takes into account the various complex "factors" or "provisions" under a specific health care plan as already verified and read from files contained at site 26. The claim payment takes into account the patient's insurance deductibles and factors already discussed in the background above. The claim amount is displayed at sites 10 or 12 regardless of any assignment provision considerations.

With this information displayed, the patient 14 and service provider 16 can read the claim payment amount that the patient's insurance carrier will pay for a particular service or collection of services. With this information now available to the patient 14 and the service provider 16, both parties are much more informed as to the economic considerations of the service or treatment transaction of the insurance claim payment which may be submitted to the patient's insurance carrier.

Both provider and patient are thus more informed and in a much better position to make a decision concerning the assignment provision of the insurance claim payment than if they did not know what the insurance carrier's payment amount would be. The service provider 16 is thus also able to render an immediate bill to the patient, if a service has been provided, for the differential between his charged fee and the reimbursement that he will receive from the insurance carrier if the displayed insurance payment does not satisfy the service provider's fee.

Depending upon a particular insurance carrier's "assignment of claim payment provisions", the assignment of the claim payment will be made by one of three parties:
(1) The patient 14

(2) The provider of the medical service 16

(3) The insurance carrier 36.

Under (3) above, insurance carriers generally assign the claim payment to either the patient 14, or to the provider 16 only if the provider 16 participates in their plan, i.e., the provider must agree to accept the insurance carrier's payment as "payment in full".

After the payment information is produced at the local entry site 10 one of the above parties, patient, provider or insurance carrier must make a decision on the assignment of claim payment.

The patient 14 or provider 16 then enters the assignment of claim payment "authorization code" at site 10 by any of the apparati shown in FIG. 4 such as keyboard 50 into the data terminal 48, thus invoking the specified party's assignment provision.

The claim is identified by the control number previously produced by the central brokerage computer 26. This claim assignment decision, together with the control number for the form is transmitted via the link 22 to the central brokerage computer 26. At the same time the local entry terminal 20 produces, at the line printer 54, a hard copy of the standard insurance form which has been filled in with the data provided by the MEDICARD 18 and input by the service provider 16. If it is necessary that the patient 14 invoke the assignment provision, he can input the signed authorization. For private insurance the patient can authorize the assignment by signing the form produced at the local entry terminal or by using device 66 to input the signature at the local entry terminal. This form can be forwarded to the patient's insurance carrier or can be stored in the files or records of the service provider 16.

At the central brokerage computer 26 the electronic insurance claim form is transmitted to the appropriate insurance carrier, such as through link 32 to insurance carrier 36. At this point, the insurance carrier processes the claim form and examines it to determine whether or not the claim payment has been assigned to the service provider 16. After the claim has been approved and if the claim payment provision has not been invoked, the insurance carrier prepares a check and mails the check directly to the patient. But, if the insurance claim assignment provision is invoked by the patient for payment directly to the service provider 16, the insurance carrier, such as 36, can effect an electronic funds transfer by means of a communication to either a bank 40, which serves the service provider 16, or to the institution 42, which has an account for the service provider 16.

The central brokerage computer 26 can further provide periodic accounting data to each of the service providers 16 as well as to the insurance carriers such as 36 and 38. This information can also be used in cost containment programs by any of the parties.

As noted above, the processing of the claim form and the transfer of funds is carried out electronically after the original entry of data. Further, the reading of the information carrying MEDICARD 18 provides a substantial amount of information for completing the claim form. Thus, the complete processing of the claim can be carried out in a period of hours since there is no need for the physical transfer of paper work. Hard copies of the claim form, however, can be produced only for file purposes at the various entities such as the local site, the computer 26 and the insurance carrier 36 or 38. This rapid processing is in contrast to the approximate four to six weeks required for the typical processing of an insurance claim form. This system also provides for numerous checks and balances to ensure accuracy and reliability for the patient, service provider and insurance carrier.

Figure 9:
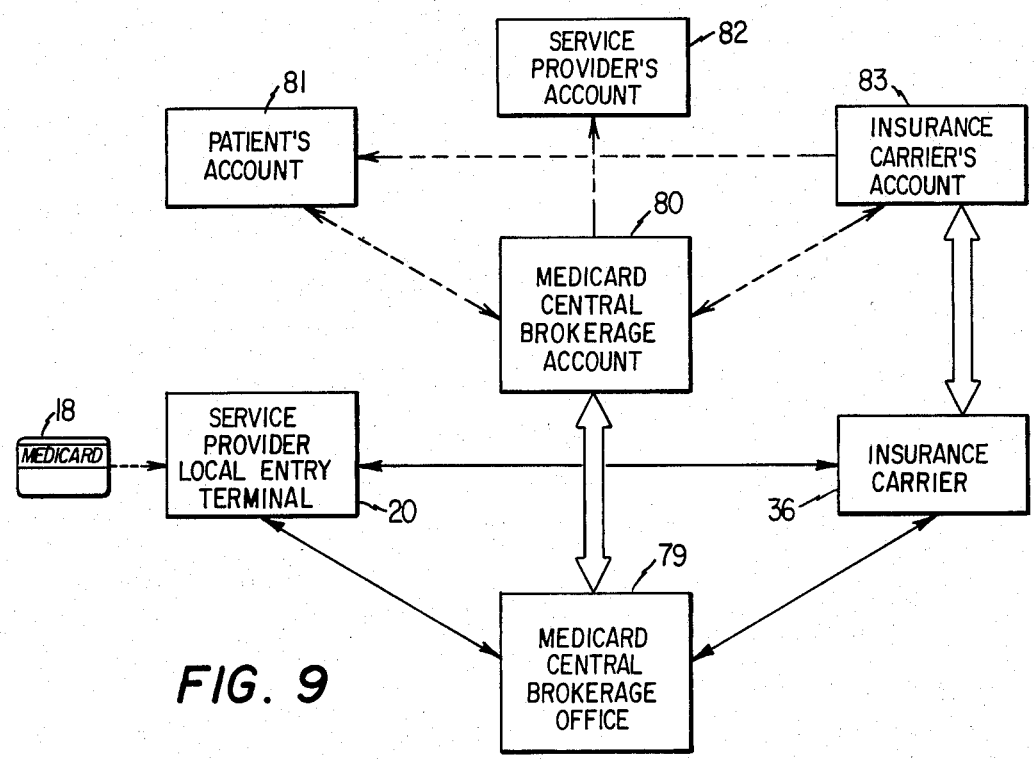
FIG. 9 is a block diagram illustrating the entities and financial accounts for the method of the present invention and showing various methods of funds transfer related to the payment for a medical service.

A further aspect of the present invention is illustrated in FIG. 9 to show the financial accounting for a medical service payment utilizing the MEDICARD 18. As described above the MEDICARD 18 is input at the local entry terminal 20 for a service provider. Information from the MEDICARD 18 together with information input by the service provider is transmitted from the terminal 20 to a central brokerage computer 26 which is within a MEDICARD central brokerage office 79. The insurance claim forms and other information can be communicated between the central brokerage office 79 and an insurance carrier, such as carrier 36.

The MEDICARD central brokerage office 79 has a corresponding MEDICARD central brokerage account 80 which can electronically transfer and receive funds. The MEDICARD central brokerage account 80 is connected to a plurality of patient's accounts represented by an account 81, a plurality of service provider's accounts, represented by account 82 and a plurality of insurance carrier accounts, represented by account 83. The insurance carrier's account 83 is also connected for a funds transfer to the patient's account 81. The patient 14 and service provider 16 have numerous options for the payment of medical services. Each of these options is described below.

Certain insurance companies do not permit the assignment of insurance claims to the service providers and under certain situations the patient does not desire to assign the claim. For this situation there are two possible routes for payment. The first comprises utilization of the MEDICARD 18 strictly as a credit card. The fee information and card identification are transmitted from the local entry terminal 20 to the MEDICARD central brokerage office 79. The office 79 then effects a funds transfer to credit the service provider's account 82 for the full amount of the fee and withdraws the corresponding amount from the patient's account 81. The patient is then billed for the fee. In a second approach, the amount of the claim payment is determined in the method described above so that the differential excess of the fee over the insurance reimbursement is determined. This differential is paid in credit card fashion by use of the MEDICARD 18, as described previously, and the insurance reimbursement is mailed from the insurance carrier to the patient. The service provider then mails a conventional statement to the patient for the amount that the patient has received from the insurance carrier.

In a second transfer situation, the patient 14 and service provider 16 have utilized the above described technique to determine the amount of insurance reimbursement which will be provided for a given service. The excess differential between the service fee and the insurance reimbursement is thus known. The MEDICARD 18 information together with the amount of the insurance reimbursement is transmitted from the terminal 20 to the MEDICARD central brokerage office 79. The insurance claim is filed from the office 79 with the insurance carrier 36. By operation of the MEDICARD central brokerage account 80, the amount of the insurance reimbursement is credited to the service provider's account 82. After the processing of the claim the claim reimbursement is transferred from the insurance carrier's account 83 to the MEDICARD central brokerage account 80. The differential between the service fee and the claim reimbursement can be handled in either of two ways. First, the differential can be paid by the patient in the credit card fashion described above through use of the MEDICARD 18. In this method the account 81 credits the differential to the service provider's account 82 and debits the patients account 81. In the second technique the patient is billed the differential amount directly by the service provider in the conventional fashion.

A further processing technique for use when the assignment provision of an insurance claim has been invoked is as follows. The insurance form is filed directly from the local entry terminal 20 to the insurance carrier 36 for processing. The reimbursement amount of the claim is then transferred from the insurance carrier's account 83 to the patient's account 81. The differential amount is billed by the service provider directly to the patient.

The patient 14 can make premium payments from his account 81 directly into the insurance carrier's account 83.

The MEDICARD central brokerage office 79 through an advance agreement between the service providers, patients, and the insurance carriers can be established as a mutual agent for funds transfer between the parties.

The brokerage account 80 can maintain a fund for the immediate payment to service providers before the completion of claim processing by the insurance carrier. The payment can be made to the service provider from the brokerage account 80 before receipt of payment from the insurance carrier. This is effectively a purchase of the service provider's accounts receivable.

Figure 10:
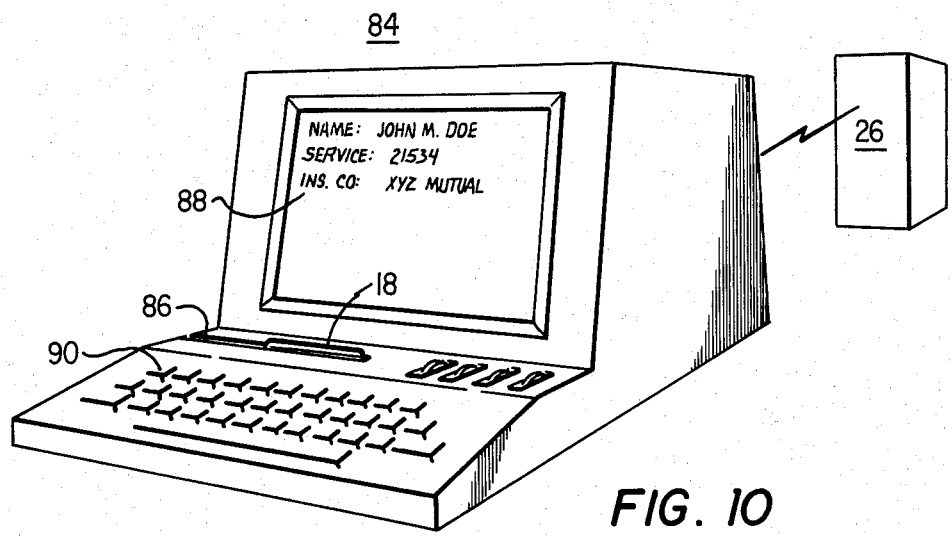
FIG. 10 is an illustration of a stand-alone reader used in conjunction with a medical reference card for reading the card and entering any necessary updates of the information on the card.

A further aspect of the present invention is illustrated in FIG. 10. A stand-alone terminal 84 is designed for reading and modifying data stored on the MEDICARD 18 without the need for access to any external data base or equipment such as the central brokerage computer 26 although it can be used in connection with the brokerage computer 26. The terminal 84 includes a slot 86 which receives the MEDICARD 18 wherein the terminal 84 electronically reads the information stored on a card. This can include both the electronically stored information and the physically imprinted information. The terminal 84 has a screen 88 for displaying the information read from the MEDICARD 18. The terminal 84 further includes a keyboard 90 for entering, updating and editing information which can be written onto the MEDICARD 18. The information produced at terminal 84 can be transmitted via computer 26 to the local terminal 20.

The terminal 84 is useful in a low-cost situation or in a situation where there are no telecommunications links for communicating with the central brokerage computer 26. In a low-cost application a service provider can determine the existence of medical coverage and all the information necessary for manually preparing an insurance claim form. The MEDICARD 18 information can further be utilized in an emergency room situation for providing the emergency personnel with clinically important medical disease and treatment information as well as all of the medical insurance information relative to the patient. The information on the card can further be utilized to assist a human organ donor recipient transplant program.

The terminal 84 can also be used in a portable application, such as in an emergency vehicle, to read vital medical information from MEDICARD 18 for an unconscious patient. A further application is for use in airports to verify flight security status for patients having the MEDICARD 18.

A stand-alone, noncommunication model of the terminal 84 is a model 700 terminal manufactured by Taltek Electronics Ltd., Montreal, Canada. A communications terminal 84 is a model 747VF, also manufactured by Taltek Electronics.

In summary, the present invention comprises a method for making a rapid determination of the validity of insurance coverage and the amount of an insurance claim payment which will be paid to a service provider or will be paid in response to a patient inquiry. This information can be determined rapidly while the patient is still at the service provider's premises so that both the service provider and patient can make a more reasoned decision concerning the assignment provision of the insurance claim under a patient's particular insurance coverage policy. This can reduce or eliminate the payment which must be made immediately by the patient. If and when MEDICARD service is provided, the insurance claim form can be electronically prepared by the service provider at a local entry terminal and transmitted via a telecommunication link to a central brokerage computer which in turn processes the form and transmits it to the appropriate insurance carrier. The insurance carrier can then, dependent upon the assignment of the claim, either send the payment to the patient directly or to the patient's bank with or without electronic funds transfer, send it to an account for the service provider, or to a central brokerage computer.

Although several embodiments of the invention have been illustrated in the accompanying drawings and described in the foregoing detailed description, it will be understood that the invention is not limited to the embodiments disclosed, but is capable of numerous rearrangements, modifications and substitutions without departing from the scope of the invention.

I claim:

1. A method for rapidly determining an insurance claim payment for a specified patient service, comprising the steps of:

storing in a system memory a file for each of the plurality of insurance carriers, each file having a set of service codes with a claim payment for each service code, storing in a system memory a code conversion table for each of said insurance carriers for converting patient treatment codes into service codes for the corresponding insurance carrier wherein said patient treatment codes correspond respectively to patient services, transmitting through a system input device codes for the name of a selected patient and a selected one of said treatment codes corresponding to said specified patient service, determining the selected patient's insurance carrier, machine reading the code conversion table for the selected patient's insurance carrier to translate the selected treatment code into the corresponding service code for the patient's insurance carrier, machine reading the file for the patient's insurance carrier to determine the claim payment for the service code which is produced by the translation of said patients treatment code, and displaying via a system output device said determined claim payment for said specified patient service for said selected patient, said input and output devices located at a common site.

2. A method as recited in claim 1 wherein said files and said conversion tables are stored at a site wherein said selected patient receives said specified patient service.

3. A method as recited in claim 1 wherein said files and said conversion tables are stored at a remote site from a local site at which said selected patient receives said specified patient service, the method including the steps of:
  transmitting said selected patient's name and said selected treatment code from said local site to said remote site and,
  transmitting said determined claim payment from said remote site to said local site.

4. A method as recited in claim 1 wherein the step of determining the selected patient's insurance carrier comprises reading a card corresponding to said selected patient and having said codes for said selected patient's insurance carrier stored thereon.

5. A method as recited in claim 1 wherein the step of determining the selected patient's insurance carrier comprises reading a file comprising the names of said patients and the insurance carrier for each said patient.

6. A method as recited in claim 1 wherein the step of transmitting through a system input device the name for a selected patient and a selected one of said treatment codes comprises the steps of:
  machine reading a card having stored therein at least a code for the name of the selected patient, and
  entering said selected treatment code into said system input by use of a manually operated device.

7. A method for rapidly verifying insurance coverage and determining an insurance claim payment for a specified patient service at a local site, comprising the steps of:
  storing in a remote site system memory a plurality of patient files, each patient file including codes for at least the patient's name, insurance carrier and type of insurance coverage,
  storing in said remote site memory a file for each of a plurality of insurance carriers, each file having a set of service codes with a claim payment schedule for each service code,
  storing in said remote site memory a code conversion table for each of said insurance carriers for converting patient treatment codes into service codes for the corresponding insurance carrier wherein said patient treatment codes correspond respectively to patient services,
  transmitting through a system input device at said local site the name for a selected patient and a selected one of said patient treatment codes corresponding to said specified patient service,
  communicating codes for at least said selected patient name and said selected treatment code from said local site to said remote site,
  machine reading at said remote site the patient file corresponding to the selected patient's name to determine the selected patient's insurance carrier and to determine the validity of the patient's insurance coverage,
  machine reading the code conversion table for the selected patient's insurance carrier to translate said selected treatment code into the corresponding service code for the selected patient's insurance carrier,
  machine reading the file for the selected patient's insurance carrier to determine the claim payment for the service code produced by the translation of said patient treatment code,
  communicating said determined claim payment from said remote site to said local site, and
  displaying via a system output device at said local site said determined claim payment for the specified patient service for said selected patient.

8. A method as recited in claim 7 wherein the step of transmitting through a system input device at said local site comprises the steps of:
  reading a card having codes therein for at least the name of said selected patient, and
  entering said selected treatment code into said system input device by use of a manually operated device.

9. A method as recited in claim 8 including the step of reading said card to produce a code identifying the insurance carrier for said selected patient.

10. A method as recited in claim 8 including the steps of:
  transmitting an identification code for one of said cards from said local site to said remote site,
  determining at said remote site the validity of said card corresponding to said identification code,
  transmitting said validity determination from said remote site to said local site, and
  displaying said validity determination at said local site.

11. A method as recited in claim 7 including the steps of:
  preparing an electronic insurance claim form at said local site for said selected patient,
  communicating said insurance claim form from said local site to said remote site,
  communicating said insurance claim form from said remote site to the insurance carrier for said selected patient, and
  communicating a funds transfer order corresponding to said determined claim payment schedule to effect a funds transfer from said selected patient's insurance carrier to a financial account for the provider of said specified patient service.

12. A method as recited in claim 11 including the step of printing at said local site an insurance claim form corresponding to said electronic insurance claim form for said selected patient.

13. The method for rapidly determining an insurance claim payment for a specified patient service in carrying out payment therefor, comprising the steps of:
  storing in a system memory a file for each of a plurality of insurance carriers, each file having a set of service codes with a claim payment for each service code,
  storing in a system memory a code conversion table for each of said insurance carriers for converting patient treatment codes into service codes for the corresponding insurance carrier wherein said patient treatment codes correspond respectively to patient services,
  determining the insurance carrier for said selected patient,
  transmitting through a system input device codes for the name for a selected patient in a selected one of said treatment codes corresponding to said specified patient services,
  machine reading the code conversion table for the selected patient's insurance carrier to translate the selected treatment code into the corresponding service code for the patient's insurance carrier, machine reading the file for the patient's insurance carrier to determine the claim payment for the service code produced by the translation of said selected treatment code, displaying via a system output device said determined claim payment for said specified patient service for said selected patient, said input and said output devices located at a common site, and transferring the amount of said determined claim payment from an account for said selected patient's insurance carrier to an account for a provider of said specified patient service.

14. A method as recited in claim 12 including the steps of:

preparing an electronic insurance claim form by the provider of said specified patient service, and communicating said electronic insurance claim form from an office of said provider of said specified patient service to the selected patient's insurance carrier.

15. A method as recited in claim 14 wherein the step of communicating said electronic insurance claim form comprises:

telecommunicating said electronic insurance claim form from said provider's office to a central brokerage computer, and telecommunicating said electronic insurance claim form from said central brokerage computer to said selected patient's insurance carrier.

16. A method as recited in claim 13 wherein the step of transferring comprises:

transferring said determined claim payment amount from the account for said selected patient's insurance carrier to a central brokerage account, and transferring said determined claim payment amount from said central brokerage account to said account for said provider of said specified patient service.

17. A method for rapidly determining an insurance claim payment for a specified patient service in carrying out payment therefor, comprising the steps of:

storing in a system memory a file for each of a plurality of insurance carriers, each file having a set of service codes with a claim payment for each service code, storing in a system memory a code conversion table for each of said insurance carriers for converting patient treatment codes into service codes for the corresponding insurance carrier wherein said patient treatment codes correspond respectively to patient services, determining the insurance carrier for said selected patient, transmitting through a system input device codes for the name for a selected patient and a selected one of said treatment codes corresponding to said specified patient services wherein the provider of said specified patient service has a fee for said specified patient service, machine reading the code conversion table for the selected patient's insurance carrier to translate the selected treatment code into the corresponding service code for the patient's insurance carrier, machine reading the file for a patient's insurance carrier to determine the claim payment for the service code produced by the translation of said selected treatment code, displaying via a system output device said determined claim payment for said specified patient service for said selected patient, said input and output devices located at an office for said provider, communicating an electronic insurance claim form from an office of said provider to the selected patient's insurance carrier, transferring said fee amount from a central brokerage account to an account for said provider of said specified patient service, transferring a difference amount by which said fee amount exceeds said determined claim payment from an account for said selected patient to said central brokerage account, and transferring said determined claim payment amount from an account for said selected patient's insurance carrier to said central brokerage account.

18. A method as recited in claim 12 wherein the step of communicating an electronic insurance claim form comprises:

telecommunicating said electronic insurance claim form from said providers office to a central brokerage computer, and telecommunicating said electronic insurance claim form from said central brokerage computer to said selected patient's insurance carrier.

19. A method for determining the validity of insurance coverage and vital medical information for a patient, comprising the steps of: recording codes on a card for at least the following information items:

(a) patient's name,
(b) patient's blood type,
(c) patient's insurance carrier,
(d) date of patient's effective insurance coverage, entering said card into a stand-alone reader machine having a display screen, reading said card to determine said information items, and displaying said information items on said reader machine display screen.

20. A method as recited in claim 19 wherein said card has recorded thereon additional codes for:

(a) the patient's medical history,
(b) the patient's address,
(c) emergency notification for the patient's doctor and relatives,
(d) flight security status for the patient,
(e) organ donor information for the patient, and
(f) the patient's social security account number.

21. A method as recited in claim 19 wherein at least a part of said codes are permanently embossed on said card and a further part of said codes are recorded magnetically on said card to permit erasing and updating.

* * * * *